(12) United States Patent
Blus et al.

(10) Patent No.: US 11,721,501 B2
(45) Date of Patent: *Aug. 8, 2023

(54) DEVICE WITH MOVABLE BUTTONS OR SWITCHES AND TACTILE IDENTIFIER

(71) Applicant: GYRUS ACMI, INC., Southborough, MA (US)

(72) Inventors: Theodore C. Blus, Arden Hills, MN (US); Kester Julian Batchelor, Mound, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/804,016

(22) Filed: May 25, 2022

(65) Prior Publication Data

US 2022/0285107 A1    Sep. 8, 2022

Related U.S. Application Data

(63) Continuation of application No. 16/363,578, filed on Mar. 25, 2019, now Pat. No. 11,361,918.

(51) Int. Cl.
*H01H 13/70* (2006.01)
*A61B 18/14* (2006.01)
(Continued)

(52) U.S. Cl.
CPC ........ *H01H 13/70* (2013.01); *A61B 18/1442* (2013.01); *H01H 3/20* (2013.01);
(Continued)

(58) Field of Classification Search
CPC ........ H01H 15/00; H01H 15/06; H01H 15/02; H01H 15/10; H01H 1/36; H01H 15/04;
(Continued)

(56) References Cited

U.S. PATENT DOCUMENTS

| 4,181,826 A | 1/1980 | Latasiewicz |
| 4,256,931 A | 3/1981 | Palisek |

(Continued)

FOREIGN PATENT DOCUMENTS

| EP | 1852078 A1 | 11/2007 |
| EP | 1897506 A1 | 3/2008 |

(Continued)

OTHER PUBLICATIONS

"U.S. Appl. No. 16/363,578, Notice of Allowance dated Feb. 16, 2022", 9 pgs.

(Continued)

*Primary Examiner* — Ahmed M Saeed
(74) *Attorney, Agent, or Firm* — Schwegman Lundberg & Woessner, P.A.

(57) ABSTRACT

The present teachings provide for a device with a membrane and an underlying switch, an underlying switch actuator, or both that has a unique tactile pattern that is felt through the membrane when the membrane is aligned with the switch, switch actuator, or both, corresponding to the electrical state of the device. The membrane, the switch, the switch actuator or a combination thereof can be repositioned from a first position to a second position so that a different tactile feel is present through the membrane corresponding to a second electrical state.

18 Claims, 8 Drawing Sheets

(51) Int. Cl.
*H01H 9/26* (2006.01)
*H01H 25/00* (2006.01)
*H01H 3/20* (2006.01)
*A61B 18/00* (2006.01)
*A61B 17/00* (2006.01)
*H01H 3/40* (2006.01)

(52) U.S. Cl.
CPC ............ *H01H 9/26* (2013.01); *H01H 25/002* (2013.01); *A61B 2017/00376* (2013.01); *A61B 2018/00607* (2013.01); *A61B 2018/00922* (2013.01); *A61B 2018/00958* (2013.01); *A61B 2018/1452* (2013.01); *H01H 3/40* (2013.01); *H01H 2300/014* (2013.01)

(58) Field of Classification Search
CPC ...... H01H 71/58; H01H 13/70; H01H 13/702; H01H 1/10; H01H 13/14; H01H 11/00; H01H 3/02; H01H 3/12; H01H 13/48; H01H 13/20; H01H 13/64; H01H 13/703; H01H 13/88; H01H 3/40; H01H 2300/014; H01H 2217/024; H01H 2025/004; A61B 2017/00376; A61B 2018/00607; A61B 2018/00922; A61B 2018/00958; A61B 2018/1452; A61B 2017/320095; A61B 2018/00297; A61B 2018/00916; A61B 2018/00946; A61B 2017/00367; A61B 2017/00371
See application file for complete search history.

(56) References Cited

U.S. PATENT DOCUMENTS

| | | | |
|---|---|---|---|
| 4,319,099 A | 3/1982 | Asher | |
| 4,504,707 A | 3/1985 | Ochiai | |
| 4,688,569 A | 8/1987 | Rabinowitz | |
| 4,703,139 A | 10/1987 | Dunlap | |
| 4,800,878 A | 1/1989 | Cartmell | |
| 4,802,476 A | 2/1989 | Noerenberg et al. | |
| 4,846,516 A | 7/1989 | Yuh et al. | |
| 5,035,695 A | 7/1991 | Weber, Jr. et al. | |
| 5,071,426 A | 12/1991 | Dolgin et al. | |
| 5,226,904 A | 7/1993 | Gentelia et al. | |
| 5,376,765 A | 12/1994 | Holmes et al. | |
| 5,399,823 A | 3/1995 | Mccusker | |
| 5,472,442 A | 12/1995 | Klicek | |
| 5,663,532 A | 9/1997 | Dieken et al. | |
| 5,743,384 A | 4/1998 | Clark | |
| 5,762,613 A | 6/1998 | Sutton et al. | |
| 6,110,171 A | 8/2000 | Rydell | |
| 6,113,596 A | 9/2000 | Hooven et al. | |
| 6,190,386 B1 | 2/2001 | Rydell | |
| 6,193,714 B1 | 2/2001 | Mcgaffigan et al. | |
| 6,310,308 B1 | 10/2001 | Watson et al. | |
| 6,358,268 B1 | 3/2002 | Hunt et al. | |
| 6,423,918 B1 | 7/2002 | King et al. | |
| 6,551,313 B1 | 4/2003 | Levin | |
| 6,590,508 B1 | 7/2003 | Howell et al. | |
| 6,623,499 B1 | 9/2003 | Andreini et al. | |
| 6,679,882 B1 | 1/2004 | Kornerup | |
| 6,911,608 B2 | 6/2005 | Levy | |
| 7,083,620 B2 | 8/2006 | Jahns et al. | |
| 7,232,440 B2 | 6/2007 | Dumbauld et al. | |
| 7,572,990 B2 | 8/2009 | Struve, Jr. | |
| 7,687,734 B2 | 3/2010 | Weber | |
| 7,902,474 B2 | 3/2011 | Mittleman et al. | |
| 8,089,017 B2 | 1/2012 | Chen et al. | |
| 8,262,655 B2 | 9/2012 | Ghabrial et al. | |
| 8,287,534 B2 | 10/2012 | Balog | |
| 8,378,240 B2 | 2/2013 | Rajagopal et al. | |
| 8,761,846 B2 | 6/2014 | Caine | |
| 9,286,884 B2 | 3/2016 | Baker et al. | |
| 9,748,057 B2 | 8/2017 | Blus et al. | |
| 9,959,996 B2 | 5/2018 | Casparian et al. | |
| 10,796,863 B2 | 10/2020 | Stringer et al. | |
| 11,361,918 B2* | 6/2022 | Blus | A61B 18/1442 |
| 2002/0038121 A1 | 3/2002 | Rozenberg et al. | |
| 2005/0113827 A1 | 5/2005 | Dumbauld et al. | |
| 2005/0130697 A1 | 6/2005 | Dyer | |
| 2005/0187512 A1 | 8/2005 | Isola et al. | |
| 2006/0084973 A1 | 4/2006 | Hushka | |
| 2007/0049927 A1 | 3/2007 | Saltzman | |
| 2008/0086117 A1 | 4/2008 | Cao | |
| 2008/0289952 A1 | 11/2008 | Pelrine et al. | |
| 2009/0015547 A1 | 1/2009 | Franz et al. | |
| 2010/0198200 A1 | 8/2010 | Horvath | |
| 2011/0220479 A1 | 9/2011 | Zhou | |
| 2012/0116267 A1 | 5/2012 | Kimball et al. | |
| 2012/0123405 A1 | 5/2012 | Moua et al. | |
| 2014/0048397 A1 | 2/2014 | Sykes et al. | |
| 2014/0276795 A1 | 9/2014 | Batchelor et al. | |
| 2014/0276797 A1 | 9/2014 | Batchelor et al. | |
| 2014/0276799 A1 | 9/2014 | Batchelor et al. | |
| 2014/0291380 A1 | 10/2014 | Weaner et al. | |
| 2017/0323744 A1* | 11/2017 | Blus | H01H 9/26 |
| 2017/0351341 A1 | 12/2017 | Norwalk et al. | |
| 2020/0312588 A1* | 10/2020 | Blus | H01H 13/70 |

FOREIGN PATENT DOCUMENTS

| | | |
|---|---|---|
| EP | 1852078 B1 | 11/2010 |
| WO | WO-2017172082 A1 | 10/2017 |
| WO | WO-2018056571 A1 | 3/2018 |

OTHER PUBLICATIONS

Blus, Theodore, et al., "Device With Movable Buttons or Switches", Potentially Related U.S. Appl. No. 14/987,233, filed Jan. 4, 2016, 39 pgs.

Blus, Theodore, et al., "Device With Movable Buttons or Switches", Potentially Related U.S. Appl. No. 15/657,904, filed Jul. 24, 2017, 39 pgs.

Shuttleworth, Timothy, et al., "Security Systems for Containers", Potentially Related U.S. Appl. No. 15/591,351, filed May 10, 2017, 52 pgs.

* cited by examiner

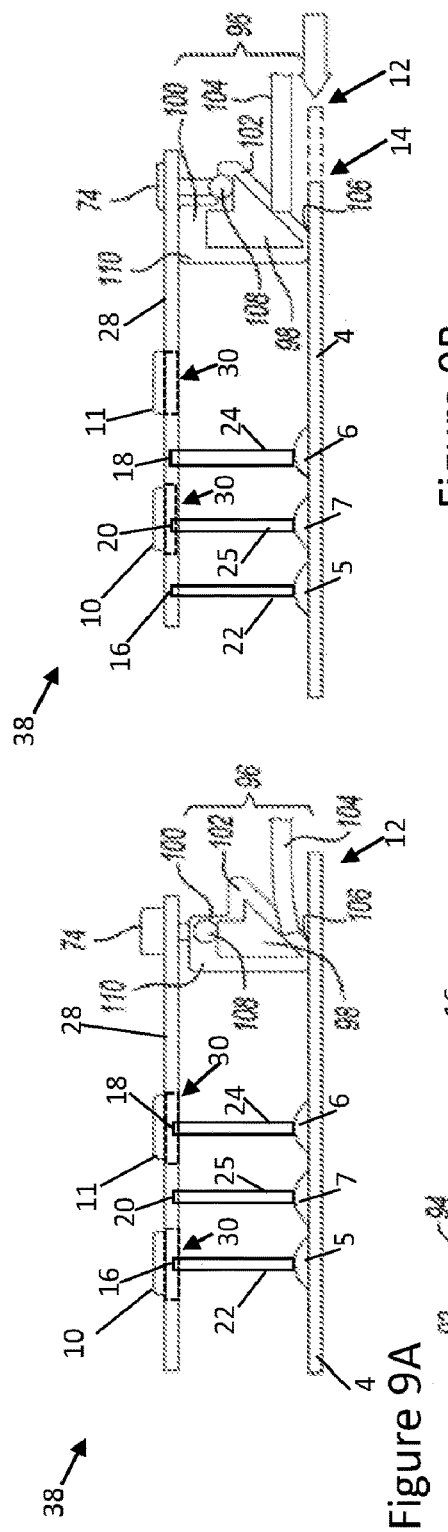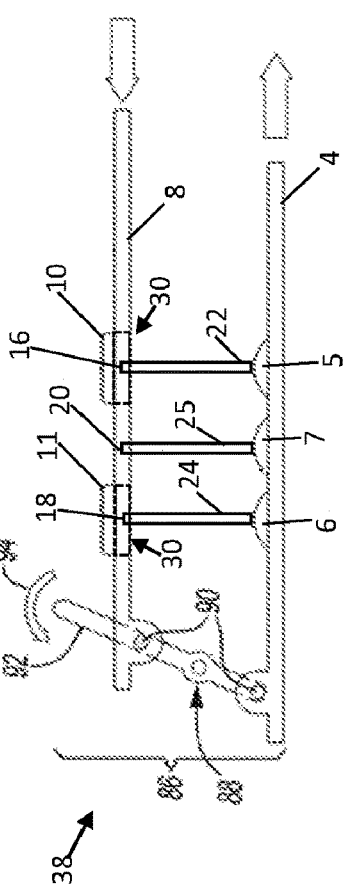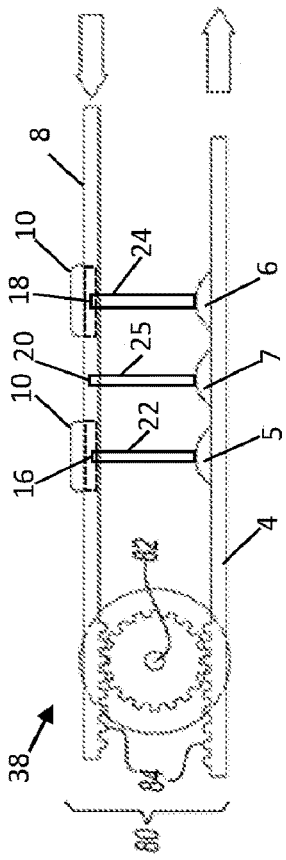

DEVICE WITH MOVABLE BUTTONS OR SWITCHES AND TACTILE IDENTIFIER

CROSS-REFERENCE TO RELATED APPLICATION

This application is a Continuation of U.S. patent application Ser. No. 16/363,578, filed on Mar. 25, 2019, and now issued as U.S. Pat. No. 11,361,918, the content of which is incorporated herein by reference in its entirety.

FIELD

The present teachings generally relate to devices, more specifically electrosurgical devices that include a circuit board switch and/or button that is repositionable between two or more positions so that two or more functional states are enabled and one or more indicators that identify each of the two or more functional states.

BACKGROUND

Typically, surgical devices have one functional element, thus if a different function is desired a surgeon will switch devices during a procedure to a device with a different function. However, some devices include a second functional element and each functional element is activated by actuating each individual button. For example, if the surgeon selects a device that has two buttons, one button activates monopolar cut and a second button activates bipolar coagulation. During surgery, it may be hard to determine which button provides which function without looking down to see which button provides a specified function. Additionally, if a device has one or more buttons with two or more functions, the surgeon may not be able to distinguish which therapy current (e.g. cut or coagulation) is provided upon actuation of the one or more buttons, which may lead to selecting the wrong function.

Examples of some electrosurgical instruments may be found in U.S. Pat. Nos. 6,110,171; 6,113,596; 6,190,386; 6,358,268; 7,232,440, and 9,748,057; and U.S. Patent Application Publication Nos. 2005/0113827; 2005/0187512; 2006/0084973; 2012/0123405; 2014/0276795; 2014/0276799, and 2017/0323744; and PCT Publication No. WO 2017/172082, all of which are incorporated by reference herein for all purposes. What is needed is a device that easily transforms between a plurality of different electrical states and functions while providing a tactile identifier of which electrical state and function that is selected. It would be attractive to have a device that can switch between two or more states and multiple states with a single button and the single button includes one or more identifiers that tactilely indicates which of the two or more states have been selected. It would be attractive to have a device that mechanically reconfigures states so that the circuitry of the device physically changes position, electrically reconfiguring the device relative to the membrane, switch actuators, switches, or a combination thereof while providing a tactile identifier that provides a particular cue for a user to feel through the sense of touch. What is needed is a device including a unique identifier that provides a tactilely readable cue that corresponds to the electrical state that will be provided upon activation of the switch.

SUMMARY

It would be attractive to have a device with a membrane and an underlying switch, an underlying switch actuator, or both that has a unique tactile pattern that is felt through the membrane when the membrane is aligned with the switch, switch actuator, or both, corresponding to the electrical state of the device. The membrane, the switch, the switch actuator or a combination thereof can be repositioned from a first position to a second position so that a different tactile feel is present through the membrane corresponding to a second electrical state.

The present teachings meet one or more of the present needs by providing: A device comprising: (a) at least a first functional state and a second functional state; (b) a selector assembly that moves between at least a first position and a second position, the selector assembly comprising: (i) one or more circuit boards with two or more electronic switches; (ii) one or more switch actuators; (iii) a shuttle in communication with the one or more circuit boards, the one or more actuators, or both to move between at least the first position and the second position; and (c) a membrane in communication with the one or more switch actuators; wherein the selector assembly in the first position is configured to provide a first functional element in the first functional state, and in the second position is configured to provide a second functional element in the second functional state; wherein each of the one or more switch actuators includes one or more identifiers, so that at least a first identifier is configured to be read through a contact portion of the membrane when the selector assembly is in the first position, and at least a second identifier is configured to be read through the contact portion of the membrane when the selector assembly is in the second position; and wherein the first functional element is activated when the one or more switch actuators with the at least first identifier is depressed, actuating a first switch of the two or more electronic switches, and the second functional element is activated when the one or more switch actuators with the at least second identifier is depressed, actuating a second switch of the two or more electronic switches.

Another possible embodiment of the present teachings comprises: An electrosurgical device comprising: (a) a frame; (b) a selector assembly that moves between a first position and a second position, the selector assembly comprising: (i) a circuit board with a first electronic switch and a second electronic switch; (ii) a first switch actuator and a second switch actuator; (iii) a shuttle in communication with the circuit board, the first switch actuator, and the second switch actuator to move between the first position and the second position; and (c) a membrane with a membrane contact area; wherein the selector assembly in the first position is configured to provide a first therapy current, and in the second position is configured to provide a second therapy current; wherein the first switch actuator includes a first identifier and the second switch actuator includes a second identifier, so that the first identifier is configured to be read through the membrane contact area when the selector assembly is in the first position, and the second identifier is configured to be read through the membrane contact area when the selector assembly is in the second position; wherein the first therapy current is activated when the first switch actuator with the first identifier is depressed, actuating the first electronic switch, and the second therapy current is activated when the second switch actuator with the second identifier is depressed, actuating a second electronic switch; wherein selector assembly includes a rotating element, the rotating element rotates between the first position and the second position; wherein the first switch actuator and the second switch actuator are connected with the rotating element so that in the first position the first switch actuator is in proximity with the membrane contact area and the second switch actuator is aligned with the first electronic switch, and in the second position the second switch actuator is in proximity with the membrane contact area and the first switch actuator is aligned with the second electronic switch in the second position; and wherein the first identifier and the second identifier are tactile patterns that are tactilely distinct from each other.

The teachings herein provide a device that mechanically changes states so that the circuitry of the device electrically changes state relative to the membrane, the switch actuators, the electronic switches, or a combination thereof to change the functional outputs of the device.

BRIEF DESCRIPTION OF THE DRAWINGS

FIG. 9A illustrates a perspective view of the selector assembly with a leaf spring mechanism in a first position;

FIG. 9B illustrates a perspective view of the selector assembly with a leaf spring mechanism in a second position;

FIG. 10 illustrates a perspective view of the selector assembly with a short throw lever assembly;

FIG. 11 illustrates a perspective view of the selector assembly with a rotating assembly.

DETAILED DESCRIPTION

Figure 1A:
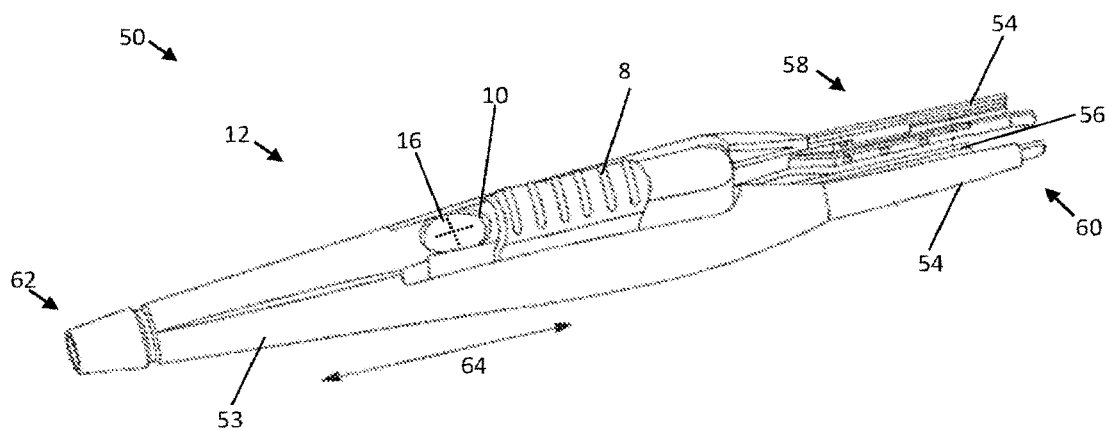
FIG. 1A is a perspective view of a surgical device in a first state.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings relate to a device that is changeable between two or more states. The device may be any device that functions to generate a signal, provide power, or both. The device may transmit a first set of signals in a first state and a second set of signals in a second state. The device may include one or more membranes with one or more membrane contact areas. The membrane contact areas may function to align with one or more switch actuators and the one or more membrane contact areas may provide two or more signals depending on the position or state of the membrane contact areas, the switch actuators, the circuit board, or a combination thereof. The one or more membrane contact areas, the one or more switch actuators, the one or more circuit boards, or a combination thereof may be movable relative to each other to create different signals so that the device provides different functions when the circuit board switches are actuated. The one or more switch actuators may include one or more identifiers. The one or more identifiers may function to provide a user a tactile identifier through the one or more membrane contact areas to indicate which state the device is in. The present teachings may relate to a surgical device and associated componentry that form an electronic, ultrasonic, or motorized surgical system or a combination thereof. The present teaching may relate to a convertible surgical device with one or more tactile identifiers.

The surgical device may be a part of a surgical system. The surgical system may be any system that includes one or more of the devices taught herein. The surgical system may include at least a surgical device with at least one functional state (e.g. configuration). The functional state may be a relative disposition or arrangement of any part of the device that moves relative to another part. For example, the selector assembly may move the membrane carrier, the switch actuators, the circuit board, or a combination thereof relative to each other or relative to a frame so that the device changes between a first functional state (or first configuration) and a second functional state (or second configuration). The surgical system may include one or more bodies as taught herein, one or more ground pads, one or more generators, one or more electrosurgical devices, one or more ultrasonic devices, one or more motorized devices, one or more adjacent body components, or a combination thereof and the teachings herein of each device, which are incorporated into the surgical system. The surgical device may be any device that may be used by a surgeon to perform a surgical procedure. The surgical device may function to be switched between two or more configurations, two or more states, or both. For example, the surgical device may be switched between an electrical state, an ultrasonic state, a motorized state, a non-powered state, or a combination thereof. The surgical device may be any device that may be switched between two or more states with one hand so that a user may switch between the states without the need for a second hand, without disrupting the procedure, or both. The surgical device may be any device and/or state that may be used ambidextrously, ambidextrously switched between states, or both. The surgical device may be used to cut, perform hemostasis, coagulate, desiccate, fulgurate, electrocautery, or a combination thereof. The surgical device may perform one or more functions. Preferably, the surgical device performs a plurality of functions. For example, the surgical device may perform a first function, second function, third function, fourth function, or more functions. The surgical device may be any device that includes bipolar capabilities, monopolar capabilities, non-electrosurgical capabilities, ultrasonic capabilities, motorized capabilities (e.g. powered movement to cut, grind, saw, drill or a combination thereof), or a combination thereof. The surgical device may provide an identifier corresponding to each functional element through a tactile interface. The tactile identifier may have a raised portion or an embossed portion. The tactile identifier may have a shape or pattern that is raised or embossed. The raised portion or embossed portion of the tactile identifier may be configured so that it can be felt or distinguished through the sense of touch. The surgical device may provide an identifier corresponding to each functional element through a tactile pattern. The surgical device may provide a tactile identifier corresponding to each functional element through a tactile interface. The tactile identifier may be positioned to be read on a user interface contact element (e.g. a membrane contact area) that, when depressed, activates a corresponding function. For example, the one or more identifiers may present a first tactile cue to signal a monopolar therapy current and present a second tactile cue to signal a bipolar therapy current. The surgical device may be used in open surgery. The surgical device may be used for non-powered surgical purposes. For example, the surgical device may be used as forceps, tweezers, or both that may be used to grip an object, an organ, a vein, skin, tissue, the like, or a combination thereof. In another example, one or more parts of the device may include a sharp edge and may be used to cut, similar to that of a scalpel. The surgical device may include a handpiece and a generator. The surgical device may have one or more therapy signals that extend between the handpiece and the generator. The hand piece may be a body.

The surgical device has a body. The body may function to connect a functional element to a user interface. The body may provide power, signals, or both to the function element. The body and one or more functional elements may be one integral piece or the functional element may be removable from the body. The body may include a power source or be connected to a power source. The body of the device may house the components that are used to make the device functional. The body of the device can be a hand piece. The body of the device can be forceps. The body of the device may be a frame. The body of the device may connect working arms, one or more functional elements, or both. The body of the device may include or be connected to one or more membrane carriers, at least one circuit board, a shuttle, one or more functional elements, a selector assembly, or a combination thereof.

The selector assembly allows the user to change between a plurality of functions of the surgical device. The selector assembly may function to change between multiple functions of the surgical device. The selector assembly may change the function of the surgical device by moving one or more membrane contact areas, one or more switch actuators, one or more circuit boards, or a combination thereof between two or more positions. The selector assembly is changeable between two or more positions so that at least one membrane contact area provides two or more functions. For example, the surgical device may perform or provide more functions than membrane contact areas that are present on the device (e.g., one contact area may activate 2 or more, 3 or more, 4 or more, or even 5 or more functions). The selector assembly may longitudinally move along the surgical device (e.g., may move along in the direction of the longitudinal axis of the device (e.g., forceps, motorized device, ultrasonic device)); rotationally move around a component of the surgical device (e.g., the selector assembly may follow the contour of the surgical device in a direction substantially perpendicular to the longitudinal axis); the selector assembly may laterally move (e.g., from side to side without following the contour of the device); or a combination thereof. The longitudinal axis as discussed herein is the dimension with the longest length. The selector assembly may move along or within one or more channels. The selector assembly may be movable by a sliding action, a leaf spring mechanism, a short throw lever assembly, a rack and pinion assembly, or a combination thereof. The selector assembly may include a portion that is located on a surface of the surgical device and a portion that extends into the surgical device. The selector assembly may change position through the use of a position change button. The position change button may be in communication with a mechanism or assembly that may allow for the selector assembly to move between positions when depressed. The selector assembly may be on the body, removably attached to a body, movable along the body, or a combination thereof. The selector assembly may include the shuttle, the one or more membrane carriers with the one or more membrane contact areas, the circuit board, a position change button, a leaf spring mechanism, a short throw lever assembly, a rotating assembly, or a combination thereof.

The device (e.g., a surgical device) may include a movable shuttle. The shuttle may be movable relative to the body of the surgical device. The shuttle may move the device between a plurality of states (e.g., electrical states). For example, the device may be moved from a first state to a second state. The device may be moved between a first state, second state, third state, fourth state, or a plurality of states. The shuttle may move along a line or axis of the device; along a surface of the device; pivot as a lever on the device; rotate as a knob on the device; or a combination thereof. The shuttle may move between positions (e.g., first, second, third, or fourth positions) as the shuttle moves along the device. The shuttle may longitudinally move along the surgical device (e.g., may move in the direction of the longitudinal axis of the device); rotationally move around a component of the surgical device (e.g., may follow the contour of the surgical device in a direction substantially perpendicular to the longitudinal axis); the shuttle may laterally move (e.g., from side to side without following the contour of the device); or a combination thereof. The shuttle may move along the longitudinal axis of the surgical device.

The shuttle may move in a direction substantially perpendicular to the longitudinal axis (i.e., laterally). The shuttle may move around a rotational axis that is substantially parallel to the longitudinal axis (i.e., rotationally). The shuttle may include one or more of a leaf spring mechanism, a short throw lever assembly, or a rotating assembly that assists in moving the shuttle. The shuttle may be in communication with one or more circuit boards, the membrane carrier, one or more switch actuators, or a combination thereof. The shuttle may be the one or more circuit boards, the one or more membrane carriers, or a combination of both. When the shuttle is in communication with the membrane carrier, the one or more circuit boards and the one or more switch actuators may be stationary relative to the frame or body When the shuttle is in communication with the one or more circuit boards, the one or more membrane contact areas may be stationary relative to the frame of the surgical device. The shuttle may also be in communication with the one or more switch actuators and move the one or more switch actuators relative to the one or more membrane contact areas and the one or more circuit boards. When the shuttle is in communication with either the one or more circuit boards or the membrane carrier, the one or more membrane contact areas and the one or more circuit boards may move relative to each other. The shuttle may have two or more positions (e.g., at least a first position and a second position). The shuttle may have a plurality of positions. The shuttle may have a first position, second position, third position, fourth position, or a plurality of positions relative to the frame or body. The shuttle in one or more of the positions as discussed herein may disable one or more of the states herein. The shuttle in a first position may disable a second electrical state, in a second position may disable a first electrical state and/or a third electrical state, or a combination thereof. For example, the shuttle in the second position may be positioned so that the first electrical state is disabled. The shuttle may help convert the surgical device between states based on the shuttle's position. For example, the shuttle in the first position may place the surgical device in the first state and when the shuttle is moved into the second position, the surgical device may be converted to the second state. The shuttle in a first position may align one or more of the membrane contact areas with one or more circuit board switches, one or more switch actuators, or both. The shuttle in a second position may misalign the one or more membrane contact areas with the one or more circuit board switches, the one or more switch actuators, or both. Aligning as discussed herein is the act of moving at least one element into proximity with another element. Alignment as discussed herein is the position of a first element arranged in proximity with a second element. For example, alignment of a membrane contact areas with a first actuator describes that the contact area is positioned relative to the first actuator so that the tactile pattern of the actuator is present through the membrane contact area, signaling that the contact area and the actuator are in alignment. The one or more membrane contact areas are in alignment with one or more circuit board switches, one or more actuators, or both in the first position or second position so that the membrane contact area, when depressed, can move into contact with the one or more actuators, one or more circuit board switches, or both. Alignment may be when the membrane contact area is linearly positioned and can move substantially perpendicularly to a switch actuator or a circuit board switch so that the switch is activated upon depression of the membrane contact area. The shuttle may be placed in two or more positions so that the one or more membrane contact areas align with or misalign with the one or more switch actuators, one or more switches, or both.

The selector assembly may include a position change button. The position change button may function to convert the device between two or more positions. The position change button may be in communication with a mechanism or assembly to convert the device between positions (e.g., from a first position to a second position). The position change button when actuated may engage a mechanism or assembly to move the selector assembly from one position to another position by moving the shuttle, the circuit board, the membrane contact area, the actuators or a combination thereof by converting mechanical potential energy into directional movement. The position change button is located on the exterior of the device. The position change button may include an actuator. The position change button may act upon a leaf spring mechanism, a short throw lever assembly, a rotating assembly, or a combination thereof.

The selector assembly may be a leaf spring mechanism. The leaf spring mechanism may convert the device between states (e.g., a first state and a second state). The leaf spring mechanism may include a position change button, an actuator block with a track, a plunger, a leaf spring, or a combination thereof. The actuator block may attach to the circuit board, shuttle, membrane carrier, the switch actuators or a combination thereof. The actuator block may have a track. The actuator block track may be on the interior, exterior, or both of the handpiece. The actuator block track may have at least one position. The position change button may be used to convert the leaf spring mechanism between positions. The position change button may include a plunger. The plunger may fit into the track of the actuator block. When the position change button is acted upon, the position change button plunger may move between two or more positions of the actuator block. When the position change button plunger moves, the actuator block may change position so that the leaf spring can push the actuator block, which is connected to the shuttle, the membrane carrier, the one or more switch actuators, the circuit board, or a combination thereof. The force of the leaf spring expanding may be converted into directional movement, moving the device into another position. When the actuator block is moved from one position to another position, the circuit board, the shuttle, the one or more switch actuators, the membrane carrier with the one or more membrane contact areas or combination thereof may be moved relative to each other through the transformation of the potential energy stored in the leaf spring into directional movement.

The selector assembly may be a short throw lever assembly. The short throw lever assembly may be used to convert the device between a plurality of states (e.g., a first state and a second state). The short throw lever assembly when actuated may change the position of the selector assembly from one position to another. The short throw lever assembly may include a lever, a fixed pivot point, one or more moving pivot points, or a combination thereof. The lever may attach to the shuttle, the circuit board, the membrane carrier, or a combination thereof at one of the one or more moving pivot points. The lever may pivot about a fixed point. When a force is put onto the lever, the lever may pivot around the fixed point pushing or pulling the circuit board, the shuttle, the membrane carrier, or a combination thereof. The short throw lever assembly may move the membrane contact area into alignment or misalignment with the circuit board switches, the one or more switch actuators, or both. The short throw lever assembly may move the selector assembly by moving the circuit board, the shuttle, the membrane carrier, or a combination thereof relative to each other, converting the device from one state to another state.

The selector assembly may be a rotating assembly. The rotating assembly may be a rack and pinion assembly. The rack and pinion assembly may be used to convert the device between a first state and a second state. The rack and pinion assembly may assist in changing the position of the selector assembly from one position to another position. The rack and pinion assembly may include a pinion gear, and one or more rack gears. The rack and pinion assembly may move the selector assembly through rotating a pinion gear in communication with one or more of the rack gears connected with the membrane carrier, the shuttle, the circuit board, or a combination thereof. The pinion gear may be connected with one or more switch actuators, so that when the pinion gear rotates, the one or more switch actuators rotate as well. When the assembly is rotated, the teeth of the pinion gear intertwine with the teeth of the rack gear, which may be connected to the circuit board, the membrane carrier, the shuttle, or a combination thereof, moving the circuit board switches, switch actuators, or both into alignment or misalignment with the one or more membrane contact areas.

The device may have one or more membranes. The one or more membranes may function to allow the impression of at least one tactile identifier to be translated from one side of the membrane to the other. The device may include one or more, two or more, three or more, four or more, or even a plurality of membranes. The one or more membranes may be one or more layers of material. For example, the membrane may be made of one or more layers of a thermoplastic polyurethane (TPU). The membrane may be disposed over an opening, fill an opening, located under an opening, or a combination thereof. The one or more membranes may be part of a user interface for activating one or more functions. The one or more membranes may include one or more membrane contact areas.

The one or more membranes may have one or more membrane contact areas. The one or more membrane contact areas may function to provide a user with a target portion of the membrane which the one or more tactile identifiers can be felt through the membrane. The device may include one or more, two or more, three or more, four or more, or even a plurality of membrane contact areas. The one or more membrane contact areas may be disposed over an opening, fill an opening, be located under an opening, or a combination thereof. The one or more membrane contact areas, when depressed, may contact one or more switch actuators, one or more circuit board switches, or both. For example, the membrane contact area may be located on the body of the device over an opening to allow a switch actuator, a circuit board switch, or both to directly contact and translate a tactile identifier into the membrane such that the tactile identifier can be read through the membrane and depressed by a user. The membrane contact area may be the portion of the membrane where a user interacts with the device to feel a tactile identifier to ascertain which state the device is in. For example, one of the circuit board switches is in communication with a membrane contact area so that the tactile identifier located on the membrane-facing surface of the circuit board switch is expressed through the membrane contact area so that the tactile identifier can be felt through the membrane contact area by the user. In another example, one of the switch actuators is in communication with a membrane contact area so that the identifier located on the membrane-facing surface of the switch actuator is translated through the membrane contact area so that the identifier can be read through the membrane contact area by the user. The one or more membrane contact areas, when depressed, may function to active or deactivate one or more functional elements. The one or more membrane contact areas may be located on the body of the device. The one or more membrane contact areas may be located on a membrane carrier. The membrane carrier may be moved relative to the frame or body, moving the one or more membranes with one or more membrane contact areas. The membrane carrier may have one opening per membrane contact area located thereon. The one or more membrane contact areas may be positioned to actuate one or more circuit board switches, one or more switch actuators, or both. The one or more membrane contact areas may be a plurality of membrane contact areas. The one or more membrane contact areas may be a first membrane contact area, a second membrane contact area, a third membrane contact area, a fourth membrane contact area, or even a fifth membrane contact area. Preferably, each membrane contact area may activate one or more circuit board switches so that a plurality of functions may be provided by the device. Preferably, the device may provide more functions than membrane contact areas present. The one or more membrane contact areas may contact (e.g., through direct contact or indirect contact) a circuit board switch (e.g., a dome or membrane) to initiate one or more of the functional elements. Each of the one or more membrane contact area may provide a different function, control a different functional element, provide multiple functions through the same functional element, or a combination thereof. The one or more membrane contact areas may be located on the body of the surgical device, on the shuttle, on a membrane carrier, or a combination thereof. The membrane contact area when aligned with a circuit board switch, an actuator, or both and depressed actuates a circuit board switch so that one or more of the functional elements of the device are activated. The circuit board switch is actuated when the membrane contact area is depressed, which completes a circuit and powers one or more of the functional elements. There may be more than one membrane contact area present on the surgical device. The one or more membrane contact areas may have a plurality of positions. For example, each of the one or more membrane contact areas may be moved between a first position and a second position. The one or more membrane contact areas may be longitudinally movable along the longitudinal axis of the device, laterally movable along a secondary dimension of the device (e.g., a direction substantially perpendicular to the longitudinal axis), rotatably movable about the rotational axis, or a combination thereof. Preferably, the one or more membrane contact areas will move about the longitudinal axis. The one or more membrane contact areas may be static. The one or more membrane contact areas may be static relative to the frame or to the shuttle. The one or more membrane contact areas may be a pliable element, non-conductive element, or both. The one or more membrane contact areas when aligned with the one or more circuit board switches (i.e., electronic switches), may contact the one or more circuit board switches, directly or indirectly, when depressed, activating one or more functional elements.

The device may include a membrane carrier. The membrane carrier may function to move the one or more membranes between positions. The membrane carrier may be moved between a first position, second position, third position, fourth position, or a plurality of positions. The membrane carrier may move along a line or axis of the device; along a surface of the device; pivot as a lever on the device;

rotate as a knob on the device; or a combination thereof. The membrane carrier may longitudinally move along the device (e.g., may move in the direction of the longitudinal axis of the device); rotationally move around a component of the surgical device (e.g., may follow the contour of the surgical device in a direction substantially perpendicular to the longitudinal axis); the shuttle may laterally move (e.g., from side to side without following the contour of the device); or a combination thereof. The membrane carrier may move along the longitudinal axis of the surgical device. The membrane carrier may move in a direction substantially perpendicular to the longitudinal axis (i.e., laterally). The membrane carrier may move around a rotational axis that is substantially parallel to the longitudinal axis (i.e., rotationally). The membrane carrier may be moved relative to the frame or body, moving the one or more membranes with one or more membrane contact areas. The membrane carrier may be in communication with one or more of a leaf spring mechanism, a short throw lever assembly, or a rotating assembly that assist in moving the shuttle. The membrane carrier may include one or more openings. The membrane carrier may include one or more, two or more, three or more, four or more, or even a plurality of openings. The one or more openings may be covered with the one or more membranes forming one or more membrane contact areas over the one or more openings. The membrane carrier may align and misalign the one or more membrane contact areas with the one or more switch actuators, the one or more circuit board switches, or both so that a particular tactile identifier is present through the membrane contact area. The membrane carrier may align the one or more membrane contact areas with the one or more switch actuators, the one or more circuit board switches, or both so that when the membrane contact area is depressed, the functional element associated with the particular tactile identifier is enabled. For example, the membrane carrier aligns the membrane contact area with the first circuit board switch, the first switch actuator, or both in the first position so that the first tactile identifier is translated through the membrane contact area so that when the membrane contact area is depressed, the first switch is closed enabling the first functional element. In another example, the membrane carrier is in a second position, aligning the membrane contact area with the second circuit board switch, the second switch actuator, or both so that the second tactile identifier is read through the membrane contact area so that when the membrane contact area is depressed, the second switch is closed enabling the second functional element.

The device may include tactile identifiers. Tactile identifiers may function to provide a user a particular tactile identifier corresponding to a specific functional element. The device may include two or more, three or more, four or more, five or more, or even a plurality of tactile identifiers. For example, a first tactile identifier corresponds with a first functional element, and a second tactile identifier corresponds with a second, different, functional element. The tactile identifiers may be any pattern, feeling, shape, density, size, or a combination thereof capable of being recognized by a user through the sense of touch. The one or more tactile identifiers may be raised or embossed so that a user may feel the tactile identifier. The tactile identifiers may be positioned in communication with one or more membrane contact areas so that the tactile identifier is capable of being read through the membrane contact area by a user. For example, a tactile identifier is pressed against the device-facing side of a membrane so that the pattern is impressed onto the user-facing side of the membrane, allowing a user to feel the tactile identifier through the membrane. In further example, a first tactile identifier is present and felt through the membrane contact area by a user in a first position, and a second tactile identifier is present and felt through the membrane contact area by the user in a second position. Both the first tactile pattern and second tactile pattern may be felt through the membrane without actuating the functional element of the device. The tactile identifiers may be located on the actuators, the switches, or both.

The device may include one or more switch actuators. The one or more switch actuators may function to actuate one or more circuit board switches when the membrane contact area is depressed. The device may include one or more, two or more, three or more, four or more, or even a plurality of switch actuators. The one or more switch actuators may be in communication with the shuttle, the one or more circuit board switches, the one or more membrane contact areas, or a combination thereof. For example, the one or more switch actuators are in communication with the shuttle to move between a first position and a second position. In another example, the one or more switch actuators are part of the one or more circuit board switches. The one or more switch actuators may include a tactile identifier. For example, a first switch actuator has a first tactile identifier located on the membrane-facing side of the actuator and is aligned with a first circuit board switch so that the first tactile identifier is read through the membrane contact area, and, upon depression of the membrane contact area, the first switch actuator contacts and closes the first circuit board switch, enabling a first functional element. In a further example, a second switch actuator has a second tactile identifier located on the membrane-facing side of the actuator and is aligned with a second circuit board switch so that the second tactile identifier is read through the membrane contact area, and, upon depression of the membrane contact area, the second switch actuator contacts and closes the second circuit board switch, enabling a second functional element.

The circuit board functions to activate or deactivate one or more of the functional elements. The circuit board functions to receive one or more user inputs and control one or more functional elements of the surgical device. There may be more than one circuit board in a surgical device. The circuit board may have surface mounted circuitry, through-hole circuitry, or both. The circuit board may have surface mounted circuitry. The circuit board may have components mounted or placed onto the surface. For example, all of the circuit componentry, including the one or more circuit board switches, are mounted on the top surface of the circuit board to allow the circuit board to be mounted flat onto the mounting surface of the device. The circuit board may be of a through-hole construction. Through-hole construction may fit the components with wire leads into holes in the circuit board. When more than one circuit board is present, the circuit boards may be movable relative to each other. For example, one circuit board may be moved over or under another circuit board so that a different function may be activated. One circuit board may be movable and one circuit board may be static relative to the frame or body. Both circuit boards may be movable. Each of the one or more circuit boards may provide a different function, control a different functional element, provide multiple functions through the same functional element, or a combination thereof.

The one or more circuit boards may be located on or within the body of the surgical device, on or within the shuttle, or both. The one or more circuit boards are used to activate a functional element of the surgical device. The one or more circuit boards have at least one switch per circuit board. The one or more circuit board switches may be surface mounted switches on the one or more circuit boards. When the circuit board switch is actuated, the circuit board switch may close a circuit of the circuit board and enable the functional element of the surgical device. There may be more than one circuit board present on the surgical device. The surgical device may include a plurality of circuit boards. For example, the surgical device has a first circuit board and a second circuit board. The first circuit board, when at least one switch is activated, enables a first functional element and the second circuit board, when activated at least one switch is activated, enables a second functional element. The surgical device may have a switch actuator, membrane contact area, or both that moves between the two circuit boards and the corresponding switches and aligns with the first circuit board and first switch when in the first position and with the second circuit board and second switch in the second position. In the first position, the second circuit board and second switch may be misaligned with the one or more switch actuators, one or more membrane contact areas, or both and in the second position, the first circuit board and first switch is misaligned with the one or more switch actuators, one or more membrane contact areas, or both. Preferably the one or more circuit boards may have a plurality of positions. For example, each of the one or more circuit boards may be moved between a first position and a second position. The one or more circuit boards may be longitudinally movable along the longitudinal axis of the device, laterally movable along a secondary dimension of the device (e.g., substantially perpendicular to the longitudinal axis), rotatably movable about the rotational axis (e.g., an axis that is parallel to the longitudinal axis), or a combination thereof. Preferably, the one or more circuit boards will move about the longitudinal axis. The one or more circuit boards may be static. The one or more circuit boards may be static relative to the body or frame, to the shuttle, to the switch actuators, or a combination thereof. There may be more than one circuit board switches on a circuit board. For example, there may be two circuit board switches located on the same circuit board (e.g., a first circuit board switch and a second circuit board switch). For example, both a first circuit board and a second circuit board may include a first circuit board switch and a second circuit board switch. When the first circuit board switch is depressed, a first function is performed and when the second circuit board switch is depressed, a second function is performed. The circuit board may include one or more switches.

The circuit board switches may enable the surgical device to activate functional elements when the switch is actuated. The circuit board may have one or more switches, two or more switches, three or more switches, four or more switches, or even a plurality of switches. The one or more switches may be a first switch, a second switch, a third switch, a fourth switch, a fifth switch, or more switches. The device may include the same number of switches as switch actuators. For example, the device may include two switch actuators and two switches. The device may include a different number of switch actuators and switches. For example, the device may include two switches and one switch actuator. In another example the device may include two switch actuators and three switches. The one or more circuit board switches may be flat, convex, concave, a dome switch, a membrane switch, an electrical switch, a capacitive sensor, a pressure sensor, or a combination thereof. The one or more circuit board switches may be a dome switch. The one or more circuit board switches may be integrated with the one or more switch actuators (e.g. the top of the switch is the switch actuator). The one or more circuit board switches interact with the one or more switch actuators when the one or more switch actuators are aligned with the circuit board switches such that when the one or more switch actuators are depressed, the switch actuators make contact with and engage the one or more circuit board switches to complete the circuit, enabling a functional element of the surgical device. The circuit board switches may be activated without being contacted. For example, depression of an activation button may create a field that triggers the circuit board switch so that a function is activated. The one or more circuit board switches and the one or more switch actuators are brought into alignment by changing the position of the selector assembly.

The state (e.g., electrical state or mechanical state) of the surgical device is changeable so that a functional element is selectively enabled. The surgical device has at least two states. Each of the states provide one or more different functions. For example, the first state is a forceps and provides a bipolar therapy current when the first circuit board switch is selectively actuated when the membrane contact area is depressed and a second state is a probe that may provide cutting and provides a monopolar therapy current when the second circuit board switch is selectively actuated when the membrane contact area is depressed. The surgical device creates a first state when the selector assembly is in the first position. When the selector assembly is in the first position, at least one circuit board switch is aligned with at least one of the switch actuators and the membrane contact area so that when the membrane contact area is depressed, the switch actuator contacts the circuit board switch on the circuit board, closing the circuit and enabling a first function.

The second state changes the surgical device (e.g., mechanically or electrically) into a secondary form to allow a second element of the surgical device to be used. The second state is created when the selector assembly is in the second position. In the second state the selector assembly is advanced to the second position where the selector assembly moves either the one or more circuit boards, the one or more switch actuators, the membrane carrier, or a combination thereof. When the circuit boards, switch actuators, or membrane carrier are moved, the previously enabled function may no longer be accessible due to the misalignment or realignment of the membrane contact area with the one or more switch actuators, the circuit board switches, or both. In the second state, one or more of the membrane contact areas may be misaligned with one or more of the circuit board switches, one or more switch actuators, or both so that the membrane contact area that is misaligned may be effectively disabled. In the second state, the selector assembly is in the second position so that the membrane contact area may be misaligned with the one or more switch actuators and the circuit board switch, so when the membrane contact area is depressed, the membrane contact area does not contact the switch actuator, the circuit board switch, or both and does not enable one or more of the functional elements. The second state of the surgical device may realign one of the membrane contact areas with one of the circuit board switches, one or more switch actuators, or both so that a functional element is selectively actuatable, which is different than the functional element selectively actuated in the first state. In the second state the shuttle is in the second position so that at least one of the membrane contact areas are aligned with another circuit board switch, switch actuator, or both, differing from the alignment in the first state so when the membrane contact area is depressed, the membrane contact area makes contact with the circuit board switch, the switch actuator, or both enabling a second functional element of the surgical device. For example, if the first functional element produces a therapy current, the second functional element may be a different therapy current. The second state of the surgical device may be a non-powered element.

The one or more functional elements are an integral part of the surgical device or a part that may be added to the surgical device so that the surgical device may be used to perform a surgical procedure. The surgical device has at least one functional element. The functional element may be actuated when the circuit is completed by depressing the one or more membrane contact areas. Preferably, the surgical device has more than one functional element. For example, the surgical device may be electrosurgical forceps where in the first state the electrosurgical forceps produce a therapy current and in the second state the surgical device would function as non-electrical forceps. Preferably, the surgical device has a plurality of functional elements (e.g., three or more, four or more, or even five or more). The functional elements may be electrical, motorized, ultrasonic, mechanical, or a combination thereof.

When the functional elements are electrical elements the functional elements use electricity to perform one or more portions of a surgical procedure. Electrical elements are functional elements that use electricity to operate. The electrical element may be an electrode, an electrical motor, an ultrasonic transducer, or a combination thereof. The first electrical element may be a motor and the second electrical element may be an electrode. The second electrical element may be an electrode, a second therapy current, a motor, an ultrasonic transducer, or a combination thereof. Preferably, the second electrical element is a second therapy current that passes through at least the second electrical element. The motor may be operated when the device is in a first position and the electrode may be activated when the device is in a second position. The surgical device may have at least one electrical element. The surgical device may have at least two electrical elements. The surgical device may have a plurality of electrical elements.

The electrical functional element of the surgical device may include one or more electrodes. Electrodes conduct electricity through the surgical device upon activation. Electrodes may conduct therapy currents. A therapy current may be a monopolar current, bipolar current, or a combination thereof. The therapy current may be used to cut, cauterize, coagulate, or a combination thereof during a surgery. The electrodes may conduct a therapy current that is used to actuate a motor.

The functional element of the surgical device may be a motor. A motor functions to move a component of the surgical device. The motor may be electrically powered, pneumatically powered, hydraulically powered, or a combination thereof. The motor may be used to cut, grind, saw, drill, or a combination thereof. For example, the motorized functional element of the surgical device may be a debrider, which has a stationary outer blade and rotating inner blade or the motorized functional element may be a second functional element such as irrigation or suction. In the first functional state, the debrider may be actuated and in the second functional state the irrigation or suction element may be actuated by an opening of a solenoid powered valve impinging on a fluid line. For example, the device in a first state may actuate a debrider function to cut a targeted area, and the device in a second state may actuate a vacuum source to remove debris and liquid from a targeted area, and in a third state may actuate an irrigation source to provide saline solution to a targeted area. The vacuum and irrigation may be obtained from a preexisting source and may be actuated by the activation of a solenoid. In another example, the device in a first state activates the debrider function and the device in a second state activates a bipolar coagulation function without activating the debrider motor.

The functional element of the surgical device may be an ultrasonic component. The ultrasonic functional element may be used to identify a targeted area, cut, coagulate, or a combination thereof. It is preferred that the ultrasonic element cuts and coagulates by converting the electrical energy to mechanical vibration that is applied to tissue. Ultrasonic capabilities can be combined with a monopolar function, a bipolar function, or both. For example, the device in a first state may be actuated to produce ultrasonic energy to cut a targeted area, and the device in a second state may actuate a bipolar therapy current to coagulate a targeted area. In a further example, the device in the first state sends ultrasonic energy to a targeted area, and in the second state sends both ultrasonic and bipolar energy to a targeted area to simultaneously cut and coagulate.

The functional element of the surgical device may be a mechanical device. A mechanical functional device is substantially free of electricity or any other power source. The mechanical element may be using the surgical device to cut, grip, probe, saw, strike, or a combination thereof.

The surgical device may be a combination device. A combination device incorporates two or more structural elements into a single device to make a tool that is capable of performing multiple functions without switching handsets.

FIG. 1A a perspective view of the electrosurgical device 50 with the shuttle 8 (along the longitudinal axis 64) in the first position 12 and the blade electrode 56 in the first functional state 58 so that the blade electrode 56 is retracted between the pair of working arms 54. When the shuttle 8 is in the first position 12 the first tactile pattern 16 is present through membrane 10 and the device is in the first functional state 58.

Figure 1B:
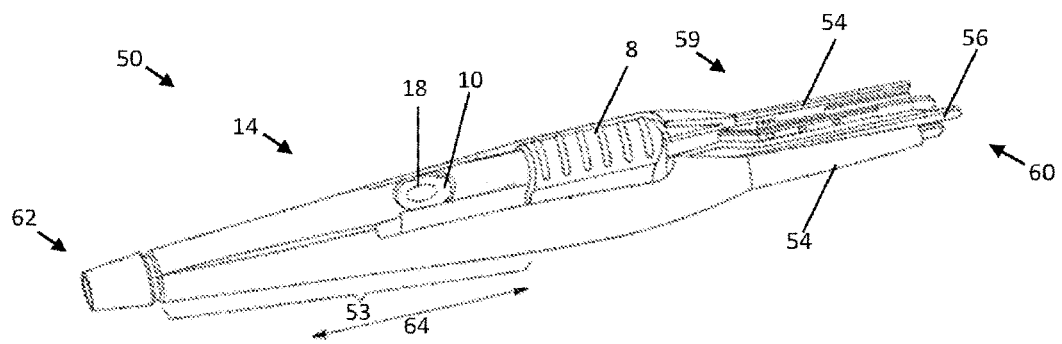
FIG. 1B is a perspective view of a surgical device in a second state.

FIG. 1B illustrates a perspective view of one example of an electrosurgical device 50. The electrosurgical device 50 is shown as forceps having a body 53 with a distal end 60 and a proximal end 62. The distal end 60 includes a pair of working arms 54 with a blade electrode 56 there between. The blade electrode 56 is advanced forward into a second functional state 59 by the shuttle 8 being moved forward into a second position 14 (i.e. along the longitudinal axis 64). In the second position 14 the second tactile pattern 18 is present through the membrane 10.

Figure 2A:
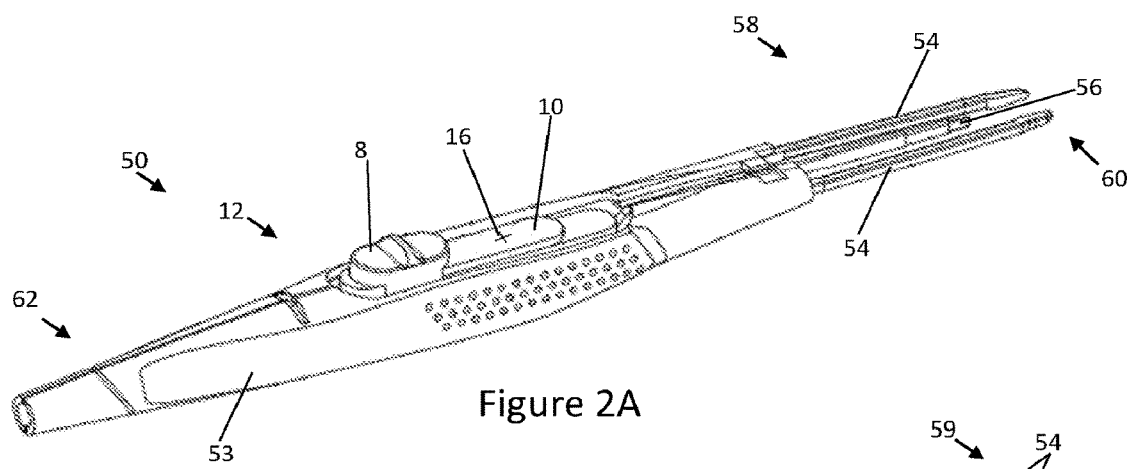
FIG. 2A is a perspective view of a surgical device in a first state.

FIG. 2A illustrates a perspective view of an electrosurgical device 50 with a shuttle 8 in the first position 12. The membrane 10 is on membrane carrier 26 so that the membrane 10 may move from the first position 12 to the second position 14. In the first position 12, the first tactile pattern 16 is present through the membrane 10 so that the first function state 58 is enabled when the membrane 10 is depressed. The blade electrode 56 is retracted between the working arms 54.

Figure 2B:
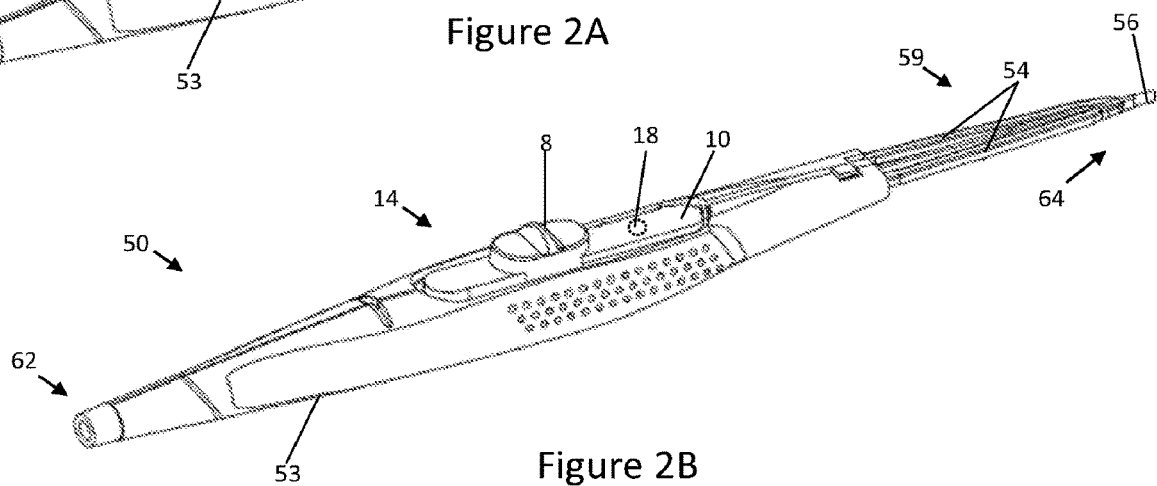
FIG. 2B is a perspective view of a surgical device in a second state.

FIG. 2B illustrates a perspective view of an electrosurgical device 50 with the shuttle 12 in the second position 14. In the second position 14, the membrane is moved into alignment with the second tactile pattern 18, which is present through the membrane 10. When membrane 10 is depressed, power is sent to the blade electrode 56. The blade electrode 56 is advanced forward into the second functional state 59 so that the blade electrode 8 extends beyond the pair of opposing working arms 54.

Figure 3A:
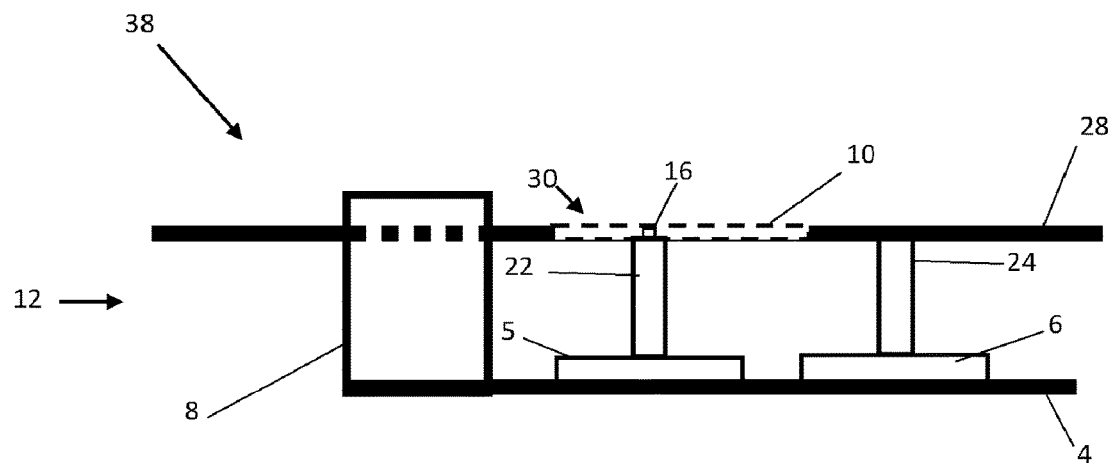
FIG. 3A is a perspective view of a selector assembly in a first position where the actuators and the switches are movable relative to the contact portion of the membrane.

FIG. 3A illustrates a selector assembly 38 including a shuttle 8 connected to a circuit board 4 in the first position 12. The opening 30 and the membrane contact area 10 are located on the frame 28. The printed circuit board 4 includes a first switch 5 and a second switch 6. As illustrated, the membrane contact area 10 is in alignment with a first switch actuator 22 and the first switch 5 so that when the membrane contact area is depressed, the switch actuator 22 contacts the switch 5 to close the circuit and enable the first functional state 58. The first tactile identifier 16 is readable through the membrane contact area 10. The second switch 6 and the second switch actuator are in misalignment with the membrane contact area 10 so that the second switch 6 cannot be actuated when the membrane contact area 10 is depressed.

Figure 3B:
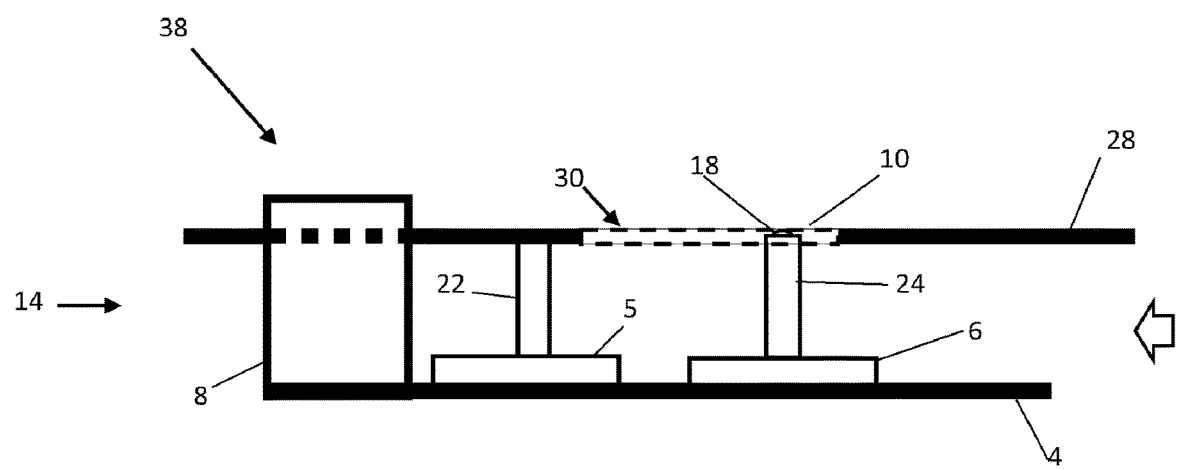
FIG. 3B is a perspective view of a selector assembly in a second position where the actuators and the switches are movable relative to the contact portion of the membrane.

FIG. 3B illustrates the selector assembly 38 including shuttle 20 and circuit board 4 in the second position 14. In the second position 14, the first switch 5 and first switch actuator 22 have been moved out of alignment with the membrane contact area 10 so that when the membrane contact area 10 is depressed, the first switch is not actuated. The second switch 6 and second switch actuator 24 are moved into alignment with the opening 30 and the membrane contact area 10 so that a second functional state 59 is enabled when the membrane contact area 10 is depressed. The second tactile identifier 18 is readable by a user through the membrane contact area 10.

Figure 4A:
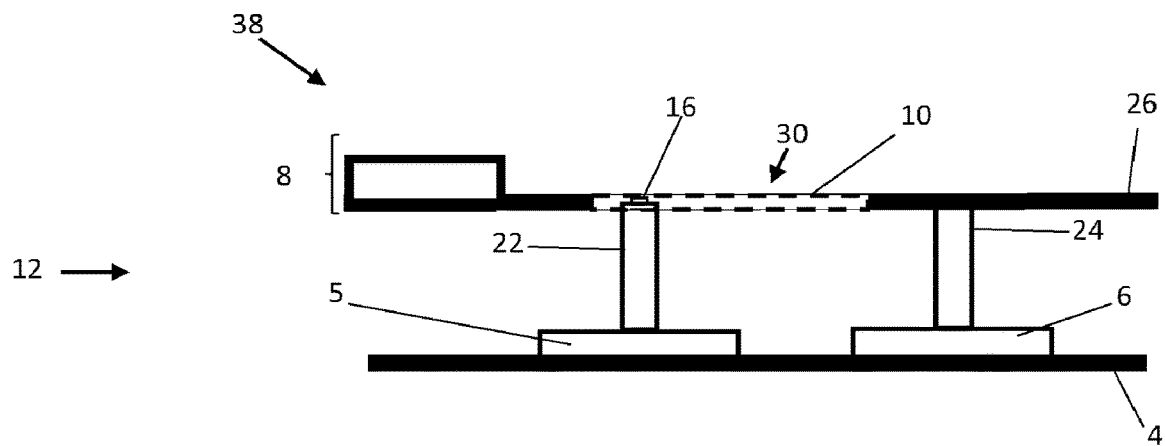
FIG. 4A is a perspective view of a selector assembly in a first position where the contact membrane is movable relative to the switches and actuators.

FIG. 4A illustrates a selector assembly 38 including shuttle 8 connected with membrane carrier 26. The opening 30 and the membrane contact area 10 ride on the membrane carrier 26 and move between the first position 12 and the second position 14. The circuit board 4 includes a first switch 5 and a second switch 6. The circuit board 4, switch actuators 22, 24, and the switches 5, 6 are stationary relative to the frame. The membrane contact area 10 is stationary relative to the shuttle 8. The shuttle 8 moves relative to the frame. In the first position 12, the membrane contact area is aligned with the first switch actuator 22 and the first switch 5, such that when the membrane contact area 10 is depressed, the first functional state is enabled. The first tactile identifier 16 is readable through the membrane contact area 10. The second switch actuator and the second switch are misaligned with the membrane contact area 10 and are covered by the membrane carrier 26 so that the second switch 6 cannot be actuated and the second tactile identifier 18 is not readable by a user.

Figure 4B:
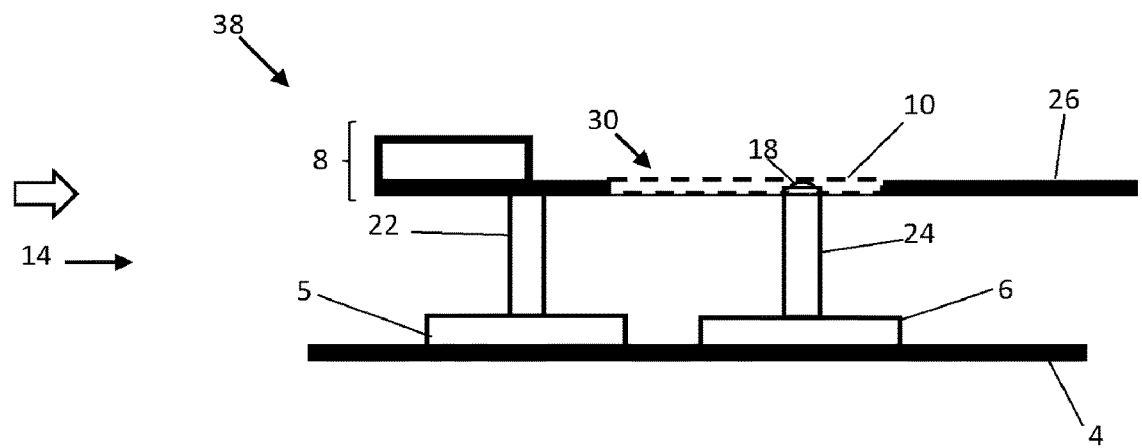
FIG. 4B is a perspective view of a selector assembly in a second position where the contact portion of the membrane is movable relative to the switches and actuators.

FIG. 4B illustrates the selector assembly 38 including shuttle 8 and membrane carrier 26 holding the opening 30 and the membrane contact area 10 are moved to the second position 14 so that the second switch actuator 24 and the second switch 6 are aligned with the membrane contact area 10. In the second position, the second tactile identifier 18 on the second switch actuator 24 is readable through the membrane contact area 10, signaling to a user that the second functional state will be actuated when the membrane contact area 10 is depressed. The first switch actuator and the first switch 5 are in misalignment with the opening 30 and the membrane contact area 10, covered by the membrane carrier 26 so that the first functional state cannot be actuated and the first tactile identifier 16 cannot be read.

Figure 5A:
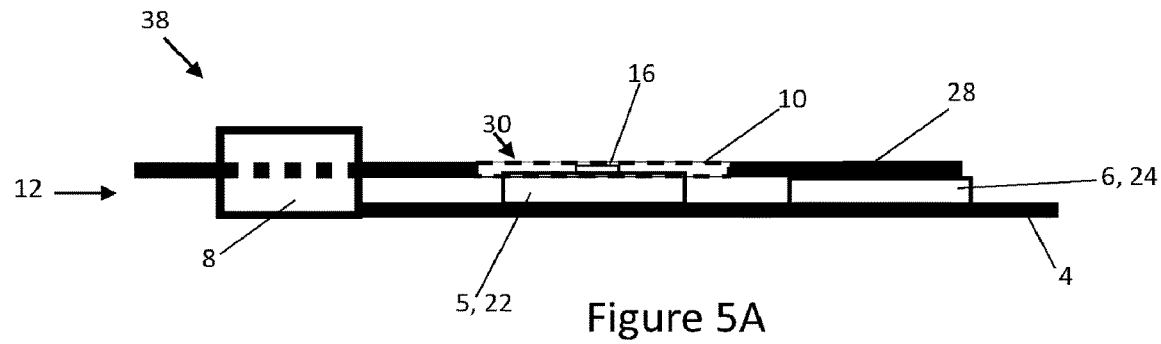
FIG. 5A is a perspective view of a selector assembly in a first position where the switches are movable relative to the contact portion of the membrane.

FIG. 5A illustrates a selector assembly 38 including a shuttle 8 connected to a circuit board 4 in the first position 12. The opening 30 and the membrane contact area 10 are located on the frame 28 and do not move with the shuttle 8 and the circuit board 4. The circuit board 4 includes a first switch 5 and a second switch 6. In this example, the first switch actuator 22 is the first switch 5, and the second switch actuator 24 is the second switch 6. As illustrated, the membrane contact area 10 is in alignment with the first switch 5 so that when the membrane contact area 10 is depressed, the switch is actuated to close the circuit and enable the first functional state 58. The first tactile identifier 16 is located on the top of switch 5 and is readable through the membrane contact area 10. The second switch 6 is not in alignment with the membrane contact area 10 so that the second switch 6 cannot be actuated when the membrane contact area 10 is depressed.

Figure 5B:
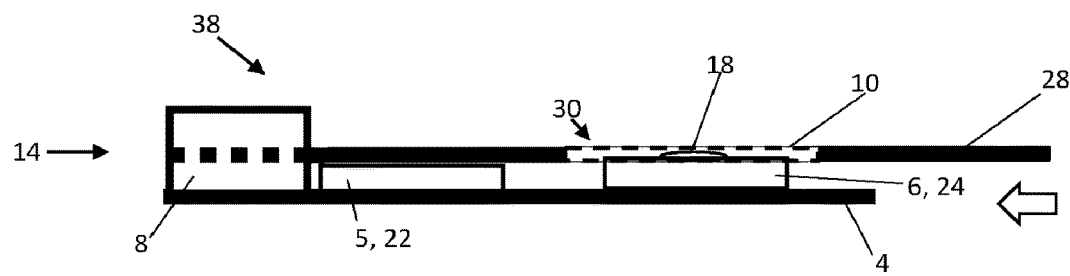
FIG. 5B is a perspective view of a selector assembly in a second position where the switches are movable relative to the contact portion of the membrane.

FIG. 5B illustrates the selector assembly 38 including shuttle 20 and circuit board 4 in the second position 14. In the second position 14, the first switch 5 has been moved out of alignment with the opening 30 and the membrane contact area 10 so that when the membrane contact area 10 is depressed, the first switch 5 is not actuated. The second switch 6 is moved into alignment with the opening 30 and the membrane contact area 10 so that a second functional state 59 is enabled when the membrane contact area 10 is depressed, actuating the second switch 6. The second tactile identifier 18 is readable by a user through the membrane contact area 10.

Figure 6A:
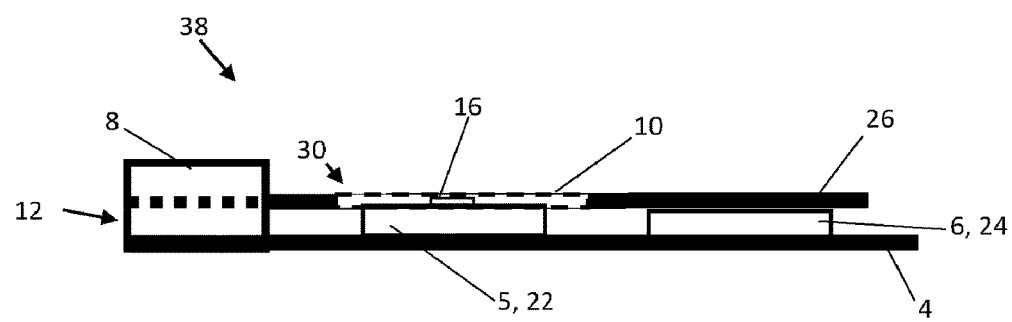
FIG. 6A is a perspective view of a selector assembly in a first position where the contact portion of the membrane is movable relative to the switches.

FIG. 6A illustrates a selector assembly 38 including shuttle 8 connected with membrane carrier 26. The membrane contact area 10 rides on the membrane carrier 26 and moves between the first position 12 and the second position 14. The circuit board 4 includes a first switch 5 and a second switch 6. The circuit board 4 and the switches 5, 6 do not move with the shuttle 8 and the membrane contact area 10. In this example, the first switch 5 is the first switch actuator 22, and the second switch 6 is the second switch actuator 24. In the first position 12, the membrane contact area 10 is in alignment with the first switch 5, such that when the membrane contact area 10 is depressed the first functional state is enabled. The first tactile pattern 16 is located on the top of the first switch 5 and is readable through the membrane contact area 10. The second switch 6 is in misalignment with the membrane contact area 10 and covered by the membrane carrier 26 so that the second switch 6 cannot be actuated and the second tactile pattern 18 is not readable by a user.

Figure 6B:
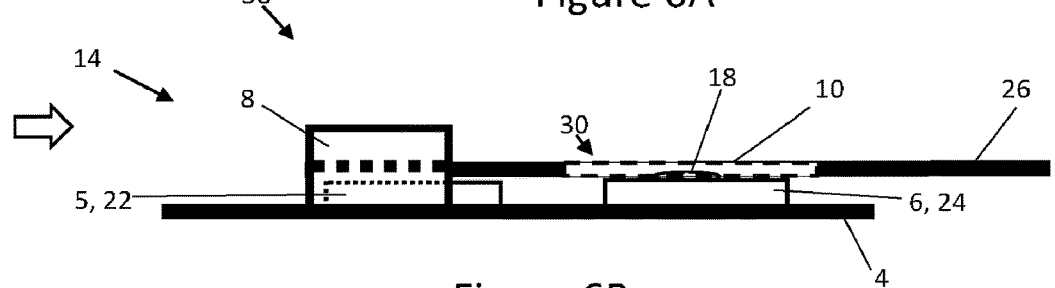
FIG. 6B is a perspective view of a selector assembly in a second position where the contact portion of the membrane is movable relative to the switches.

FIG. 6B illustrates the selector assembly 38 including shuttle 8 and membrane carrier 26 holding the opening 30 and the membrane contact area 10 are moved to the second position 14 so the second switch 6 is in alignment with the membrane contact area 10. In the second position 14, the second tactile identifier 18 on top of the second switch 6 is readable through the membrane contact area 10, signaling to a user that the second functional state will be enabled when the membrane contact area 10 is depressed. The first switch 5 is in misalignment with the membrane contact area 10 and the opening 30. The first switch 5 is covered by the membrane carrier 26 so that the first functional state cannot be actuated and the first tactile identifier 16 cannot be read.

Figure 7A:
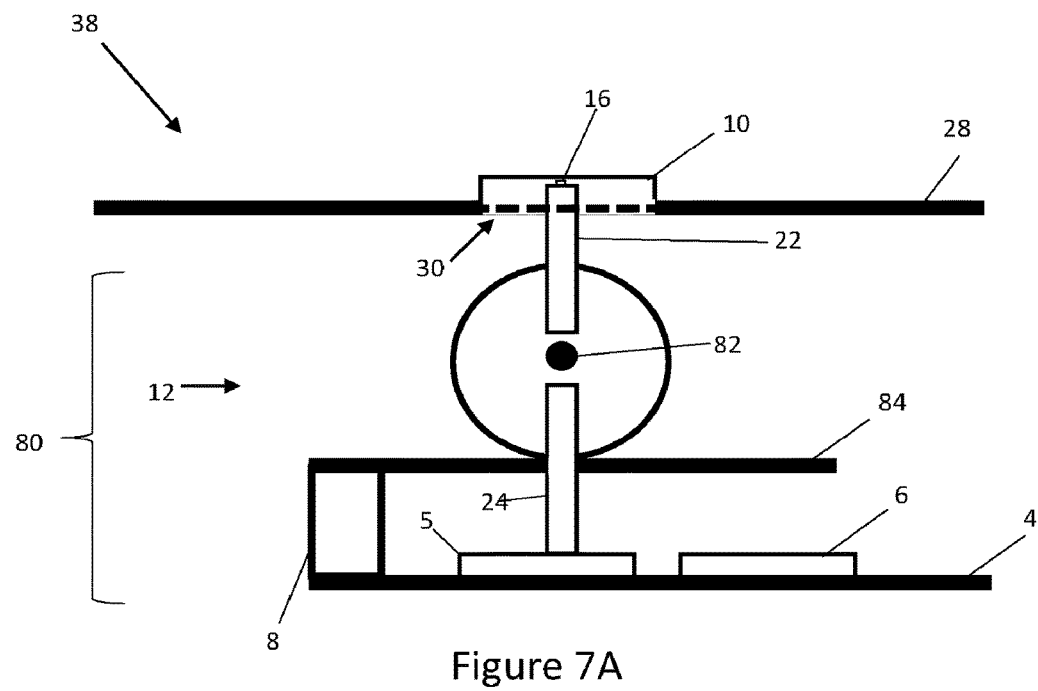
FIG. 7A illustrates a perspective view of the selector assembly with a rotating assembly in the first position.
Figure 7B:
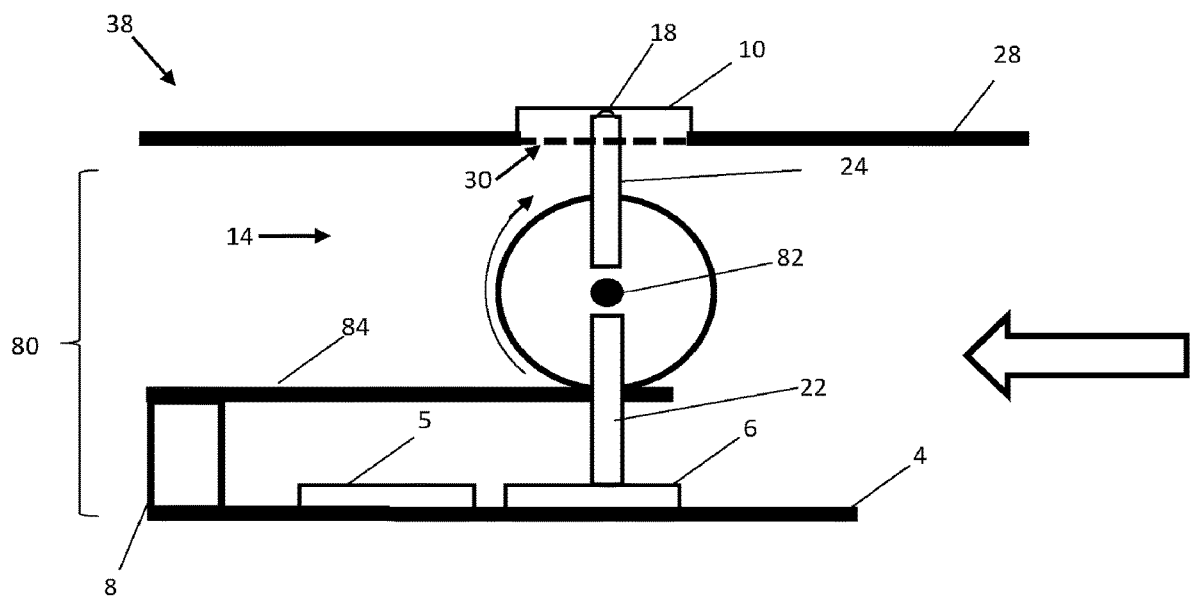
FIG. 7B illustrates a perspective view of the selector assembly with a rotating assembly in the second position.

FIGS. 7A and 7B illustrates the selector assembly 38 with the shuttle 8 connected to the circuit board 4 through a rack and pinion assembly 80. The rack and pinion assembly converts rotational movement to longitudinal movement or lateral movement. The rack and pinion assembly 80 converts the device between the first position 12 and the second position 14 by rotating the pinion to move circuit board 4 which is connected to the rack 84 by shuttle 8. The rack and pinion assembly 80 includes a pinion gear 82 and rack gears 84. The first switch actuator 22 and the second switch actuator 24 are attached to the pinion 180 degrees apart. As the pinion gear 82 rotates, the rack gear 84 laterally move the shuttle 8 and circuit board 40 in the same direction placing the device into the second position 14, aligning or misaligning the first switch actuator 22 and the first tactile identifier 16, or the second switch actuator 24 and the second tactile identifier 18 with the membrane contact area 10.

FIG. 7A illustrates the selector assembly 38 in the first position 12 with the first switch actuator with the first tactile identifier 16 aligned with the opening 30 and the membrane contact area 10. The first tactile identifier 16 located on the first switch actuator 22 is read through the membrane contact area 10. The second switch actuator 24 is positioned in communication with the first switch 5. When the membrane contact area 10 is depressed the second switch actuator 24 presses into the first switch 5, closing the circuit and enabling the first functional state 58. The second switch 6 is free from alignment with the first switch actuator 22 and the second switch actuator 24.

FIG. 7B illustrates the selector assembly 38 in the second position 14 with the second switch actuator 24 with the second tactile identifier 18 aligned with the opening 30 the membrane contact area 10. The second tactile identifier 18 is readable through the membrane contact area 10. The first switch actuator 22 is rotated 180 degrees from the membrane contact area 10 into alignment with the second switch 6 when the selector assembly is moved from the first position 12 to the second position 14. As the pinion turns, the rack moves the circuit board carrying the first switch 5 and the second switch 6. The second tactile identifier 18 on the second switch actuator 24 is read through the membrane contact area, so that when the membrane contact area 10 is depressed, the first switch actuator 22 presses into the second switch 6, closing the circuit and enabling the second functional state 59.

Figure 8A:
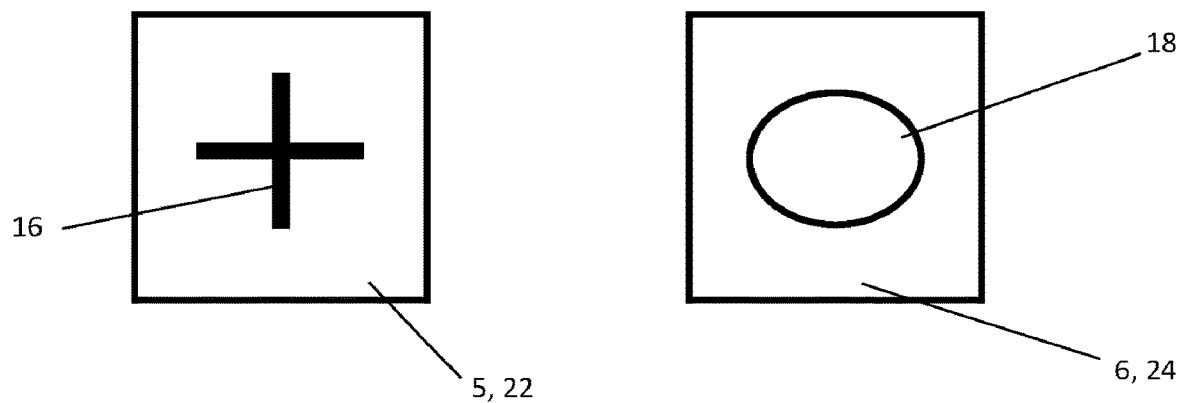
FIG. 8A illustrates a top-down view of the first and second switch and/or switch actuator with a first tactile pattern and a second tactile.
Figure 8B:
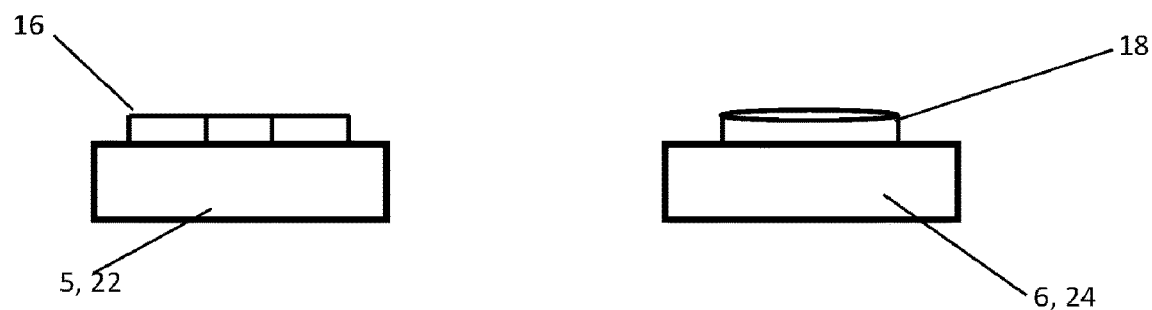
FIG. 8B illustrates a side view of the first and second switch and/or switch actuator with a first tactile pattern and a second tactile.

FIG. 8A illustrates a top view of the first switch/actuator 5, 22 and the second switch/actuator 6, 24. The first switch/actuator includes one example of a first tactile identifier 16, and the second switch/actuator 6, 24 includes one example of a second tactile identifier 18. FIG. 8B illustrates a side view of the first switch/actuator 5, 22 and the second switch/actuator 6, 24. Each of the tactile identifiers project from the top surface of the switch/actuator so that when the membrane contact area is positioned with a particular switch/actuator, the tactile pattern pushes through the membrane so that a user can feel a specific identifier associated with a specific functional element (e.g. the first functional state corresponds with the first tactile identifier and the second functional state corresponds with the second tactile identifier).

FIG. 9A illustrates the selector assembly 38 in the first position 12. The selector assembly 38 is connected to the circuit board 4 through a leaf spring mechanism 96. In this example, the circuit board 4 acts as a shuttle 8 for the switches 5, 6, 7 and switch actuators 22, 24, 25. In the first position 12, the membrane contact areas 10, 11 are located on the frame 28 and are aligned with the switches 5, 6. The first tactile identifier 16 is readable through the membrane contact area 10 and the second tactile identifier 18 is readable through the membrane contact area 11. When membrane contact areas 10, 11 are depressed, the switch actuators 22, 24 will contact switches 5, 6, respectively. No membrane contact areas are aligned with switch 7. The selector assembly includes a position change button 74 which is in communication with the leaf spring mechanism 96. The leaf spring mechanism 96 includes an actuator block 98 with a track 110, a plunger 108, and a leaf spring 104. The actuator block 98 attaches to the circuit board at region 106. The track 110 of the actuator block 98 has a top position 100 and a side position 102. The plunger 108 is connected to the position change button 74 and fits into the positions of the actuator block 100, 102 so when the position change button 74 is acted upon in direction 52, the plunger 108 moves from the top position 100 to the side position 102. When the plunger 108 moves, the leaf spring 104 pushes the actuator block 98, which is connected to the circuit board 4 at 106, converting the device into the second position (shown in FIG. 9B). When the actuator block is moved from the first position 12 to the second position, the circuit board 4 is moved relative to the membrane contact areas 10, 11. To move the device back to the first position, the position change button 74 can be actuated, causing the plunger 108 to move about the track 110 of the actuator block 98 clockwise so that the plunger 108 returns to the first position.

FIG. 9B illustrates the selector assembly 38 in the second position 14. The selector assembly 38 is connected to the circuit board 4 through the leaf spring mechanism 96. The leaf spring mechanism 96 moves the circuit board 4 from the first position 12 to the second position 14. The membrane contact areas 10, 11 are located on frame and are stationary relative to the circuit board. In the second position, membrane contact area 11 is misaligned with all of the switches 5, 6, 7. The first switch 5 and second switch 6 are not aligned with the membrane contact areas. The first membrane contact area 10 is aligned with the third switch 7 and third switch actuator 25 in the second position so that the third tactile identifier 20 is readable through the first membrane contact area 10. When the first membrane contact area 10 is depressed, switch actuator 25 contacts switch 7, closing the circuit and enabling a designated function. The leaf spring assembly 96 converts the device from the first position 12 to the second position 14 through actuating the position change button 74. The position change button 74 depresses the plunger 108 causing the leaf spring mechanism 96 to relieve tension on the leaf spring 104 which expands and moves the circuit board 4 laterally by pushing the actuator block 98, which is connected to the circuit board 40 at 106, placing the device in the second position 14. When the position change button 74 is depressed, the plunger 108 moves along the track 110 of the actuator block 98 from the top position 100 to the side position 102. The circuit board 4 moves relative to the membrane contact areas 10, 11.

FIG. 10 illustrates the selector assembly 38 connected to the circuit board 4 through a short throw lever assembly 86 where the shuttle 8 holds the membrane contact areas 10, 11 and aligns the contact areas with switches 5, 6 in the first position 12, so that when the membrane contact areas 10, 11 are depressed, the switch actuators 22, 24 will contact the switches 5, 6, respectively. In the first position 12, the third switch 7 is not aligned with either of the membrane contact areas 10, 11. The short throw lever assembly 86 includes a lever 92, a fixed pivot point 88 that the lever rotates about, and moving pivot points 90 at the circuit board 4 and the shuttle 8, respectively. The short throw lever assembly 86 converts the device between positions when moved in the 94 direction by laterally moving the shuttle 8 holding the membrane contact areas 10 and 11 and the circuit board 4 in the opposite directions. The shuttle 8 and the circuit board 4 are connected by the lever 92 at moving pivot points 90, so when the short throw lever assembly 86 is acted upon, the lever 92 pivots about the fixed point 88, moving the shuttle 8, which holds the membrane contact areas 10, 11 and switches 5, 6, 7 into aligned or misaligned.

FIG. 11 illustrates the selector assembly 38 as a rack and pinion assembly 80 connected to the circuit board 4 and the shuttle 8. The rack and pinion assembly 80 converts the device between the first position 12 and the second position 14 by moving the shuttle 20, carrying membrane contact areas 10, 11 and the circuit board 4 relative to each other. The rack and pinion assembly 80 includes a pinion gear 82 and a pair of rack gears 84, each attached to the circuit board 4 and the shuttle 8. As the pinion gear 82 rotates, the rack gears 84 laterally move the shuttle 20 and circuit board 4 in the opposite direction, placing the device into a second position (not shown), aligning and/or misaligning the membrane contact areas 10, 11 with the switch actuators 22, 24, 25 and switches 5, 6, 7. In the position shown, membrane contact areas 10, 11 are aligned with switches 5, 6, respectively, so when the membrane contact areas are depressed, membrane contact area 10 will contact switch actuator 22 closing switch 5 and membrane contact area 11 will contact switch actuator 24 closing switch 6. Switch 7 and switch actuator 25 are not aligned with either membrane contact area.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A device comprising:
    at least a first functional state and a second functional state;
    a selector assembly that moves between at least a first position and a second position, the selector assembly comprising:
        one or more circuit boards; and
        one or more switch actuators; and
    a membrane in communication with the one or more switch actuators;
    wherein the selector assembly in the first position is configured to provide a first functional element in the first functional state, and in the second position is configured to provide a second functional element in the second functional state;
    wherein each of the one or more switch actuators includes one or more identifiers, so that at least a first identifier is configured to be read through a contact portion of the membrane when the selector assembly is in the first position, and at least a second identifier is configured to be read through the contact portion of the membrane when the selector assembly is in the second position; and
    wherein the first identifier and the second identifier comprise first and second tactile patterns, respectively, that are tactilely distinct from each other.

2. The device of claim 1, wherein the selector assembly further comprises a shuttle in communication with the one or more circuit boards, the one or more switch actuators, or both to move between at least the first position and the second position.

3. The device of claim 2, wherein the one or more circuit boards include two or more electronic switches.

4. The device of claim 3, wherein the first functional element is activated when the one or more switch actuators with the at least first identifier is depressed, actuating a first switch of the two or more electronic switches, and the second functional element is activated when the one or more switch actuators with the at least second identifier is depressed, actuating a second switch of the two or more electronic switches.

5. The device of claim 3, wherein a first switch of the two or more electronic switches includes a first switch actuator of the one or more switch actuators, and a second switch of the two or more electronic switches includes a second switch actuator of the one or more switch actuators.

6. The device of claim 5, wherein the first identifier is located on the first switch actuator and the second identifier is located on the second switch actuator.

7. The device of claim 5, wherein the shuttle is connected to the one or more circuit boards to move the one of the one or more circuit boards between the first position and the second position relative to the contact portion of the membrane.

8. The device of claim 2, wherein the shuttle is connected with a first switch actuator of the one or more switch actuators with the first identifier and a second switch actuator of the one or more switch actuators with the second identifier, and wherein the shuttle is configured to move the first switch actuator and the second switch actuator between the first position and the second position relative to the contact portion of the membrane.

9. The device of claim 2, wherein one actuator of the one or more switch actuators includes the first tactile pattern and the second tactile pattern and the shuttle is connected with the one or more circuit boards.

10. The device of claim 2, wherein the membrane is stationary relative to a frame and the shuttle is configured to move the one or more circuit boards, relative to the frame, between the first position and the second position.

11. The device of claim 1, wherein the selector assembly includes a rotating element, the rotating element rotatable between the first position and the second position.

12. The device of claim 1, wherein the device is an electrosurgical device, and the electrosurgical device provides a first therapy current in the first position and a second therapy current in the second position.

13. A device comprising:
a frame;
a selector assembly that moves between a first position and a second position, the selector assembly comprising:
a circuit board with a first electronic switch and a second electronic switch;
a first switch actuator;
a second switch actuator; and
a selector element in communication with the circuit board, the first switch actuator, and the second switch actuator to move between the first position and the second position; and
a membrane with a membrane contact area;
wherein the selector assembly in the first position is configured to provide a first therapy current, and in the second position is configured to provide a second therapy current;
wherein the first switch actuator includes a first identifier and the second switch actuator includes a second identifier, so that the first identifier is configured to be read through the membrane contact area when the selector assembly is in the first position, and the second identifier is configured to be read through the membrane contact area when the selector assembly is in the second position; and
wherein the first identifier and the second identifier are tactile patterns that are tactilely distinct from each other.

14. The device of claim 13, wherein the selector element comprises a shuttle.

15. The device of claim 13, wherein the first therapy current is activated when the first switch actuator with the first identifier is depressed, actuating the first electronic switch, and the second therapy current is activated when the second switch actuator with the second identifier is depressed, actuating the second electronic switch.

16. A device comprising:
a selector assembly that is configured to move between a first position corresponding to a first functional state of the device and a second position corresponding to a second functional state of the device, the selector assembly comprising:
a circuit board with a first electronic switch and a second electronic switch;
a first switch actuator;
a second switch actuator; and
a control element in communication with the circuit board, the first and second switch actuators, or both to move between the first position and the second position; and
a membrane;
wherein a first tactile identifier is configured to be felt through the membrane when the selector assembly is in the first position, and a second tactile identifier that is tactilely distinct from the first tactile identifier is configured to be felt through the membrane when the selector assembly is in the second position.

17. The device of claim 16, wherein the membrane is in communication with the first and second switch actuators.

18. The device of claim 16, wherein the selector assembly in the first position is configured to provide a first functional element in the first functional state, and in the second position is configured to provide a second functional element in the second functional state.

* * * * *